United States Patent [19]
McCary et al.

[11] Patent Number: 6,077,272
[45] Date of Patent: Jun. 20, 2000

[54] DETECTION OF INTRAOCULAR SURGICAL SCISSORS

[75] Inventors: Brian Douglas McCary, St. Louis; John Joseph Weidenbenner, Ballwin, both of Mo.

[73] Assignee: Bausch & Lomb Surgical, Inc., Claremont, Calif.

[21] Appl. No.: 08/916,851

[22] Filed: Aug. 22, 1997

[51] Int. Cl.[7] .................................... A61F 9/00
[52] U.S. Cl. ..................... 606/107; 606/167; 606/174
[58] Field of Search ........................... 606/107, 167, 606/205, 170, 171, 174, 159, 1, 4–6, 166, 180, 169; 604/19, 22; 313/293; 330/129, 132; 333/19

[56] References Cited

U.S. PATENT DOCUMENTS 5,688,235  11/1997  Sakurai et al. ....................... 606/169
5,690,641  11/1997  Sorensen et al. ..................... 606/107
5,716,363   2/1998  Josephberg ........................... 606/107

Primary Examiner—Glenn K. Dawson
Attorney, Agent, or Firm—Grant D. Kang

[57] ABSTRACT

An apparatus and method for determining the motor type of an electric intraocular surgical handpiece. A circuit including a voltage divider, opto-isolators and amplifiers receives signals from the motor of the handpiece to determine its type. The circuit provides a signal, which can be visual or auditory, to the user concerning the motor type of the handpiece so that the user may choose the proper controls compatible with the motor type.

4 Claims, 1 Drawing Sheet

Microfiche Appendix Included
(3 Microfiche, 32 Pages)

DETECTION OF INTRAOCULAR SURGICAL SCISSORS

MICROFICHE APPENDIX

This application includes a microfiche appendix which is a copy of the provisional application under which priority is claimed and updated source code. The total number of microfiche is 3, and the total number of frames are 32.

BACKGROUND OF THE INVENTION

This invention relates to an improved control system for an intraocular surgical instrument that can be used with microsurgical scissors, forceps, knives and the like. More particularly, this embodiment of the invention relates to an apparatus for detecting intraocular surgical scissors. More particularly, this embodiment of the invention relates to an apparatus for detecting and distinguishing between different types of intraocular surgical scissors.

The invention will be described in connection with its preferred use as a portion of the control system for intraocular surgical scissors. The use of intraocular surgical scissors is well known. While manually operated scissors are still in widespread use worldwide, the use of surgical scissors with electric motor drive is also widespread. Electrical motor driven scissors are divided into two well known types based upon the type of drive, those that are solenoid actuated and those that are driven by a direct current motor or proportional control.

Most intraocular scissors have design similarities in which a pair of cutting blades extend from the end of a tubular needle with one blade being fixed and the opposite opposing blade end being reciprocated between an open and a closed position with respect to the fixed blade. This reciprocating motion is accomplished through the action of one of the driving systems such as, for example, the manual or electric motor drive.

Electric motor drivers of either rotary or linear solenoid type activate scissor closure by controlled transfer of the motor energy to the movable blade. The scissors may be of the vertical design, the guillotine or parallel blade type, the angled or horizontal-style or of other design or the scissors may be replaced by other instruments that operate similarly. The linear solenoid type provides a reciprocating action in which the electrical actuation of a solenoid causes the movable blade to move to the closed position in relation to the fixed blade and then, usually through the operation of a spring, to return to the open position. The rotary electric motor drive may also be considered as a "proportional-cut" mode of operation as the motor is typically a stepper or rotary motor. The motion of the movable blade is controlled by the surgeon and the rate and amount of closure of the blade is proportional to the rate and amount of movement of the control by the surgeon.

It may be easily seen that the operation of the Different electrical motor drives requires different controls and that connection of the wrong control system could cause problems.

SUMMARY OF THE INVENTION

The present invention includes a detection apparatus that determines, when an intraocular surgical scissors handpiece is connected to the control system, whether the handpiece is of the rotary drive or solenoid drive type. The detection apparatus provides a signal to the software control system to advise the surgeon of the type of handpiece connected.

The present invention provides an apparatus to detect the type of drive required by a connected intraocular surgical scissors handpiece. The apparatus includes a voltage divider, a pair of oppositely biased amplifiers and an opto-isolator with each of the amplifiers. When a handpiece is connected, the voltage across the voltage divider is changed in a positive or negative amount depending upon the handpiece motor drive type, changing the bias on each of the amplifiers so that the amplifier corresponding to the motor drive type is forward biased to provide a signal through the opto-isolator to the software control system. The software control system then advises the surgeon through visual means, such as notices on a cathode ray tube or a system of lights, through the use of computer created voice messages or through buzzers, bells or whistles.

The present invention further includes a method for determining the type of motor control required for a connected handpiece such as the preferred intraocular surgical scissors handpiece. The method includes the steps of applying a voltage across a voltage divider to the input of a first and a second amplifier, connecting a handpiece, changing the voltage across the voltage divider indicative of the handpiece motor drive type, forward biasing one of the first and second amplifiers as a result of changing the voltage across the voltage divider and providing a signal to the control system indicative of the handpiece motor drive type. The method may also include providing a visual indication of the handpiece motor drive type.

DETAILED DESCRIPTION OF THE DRAWINGS

Figure 1:
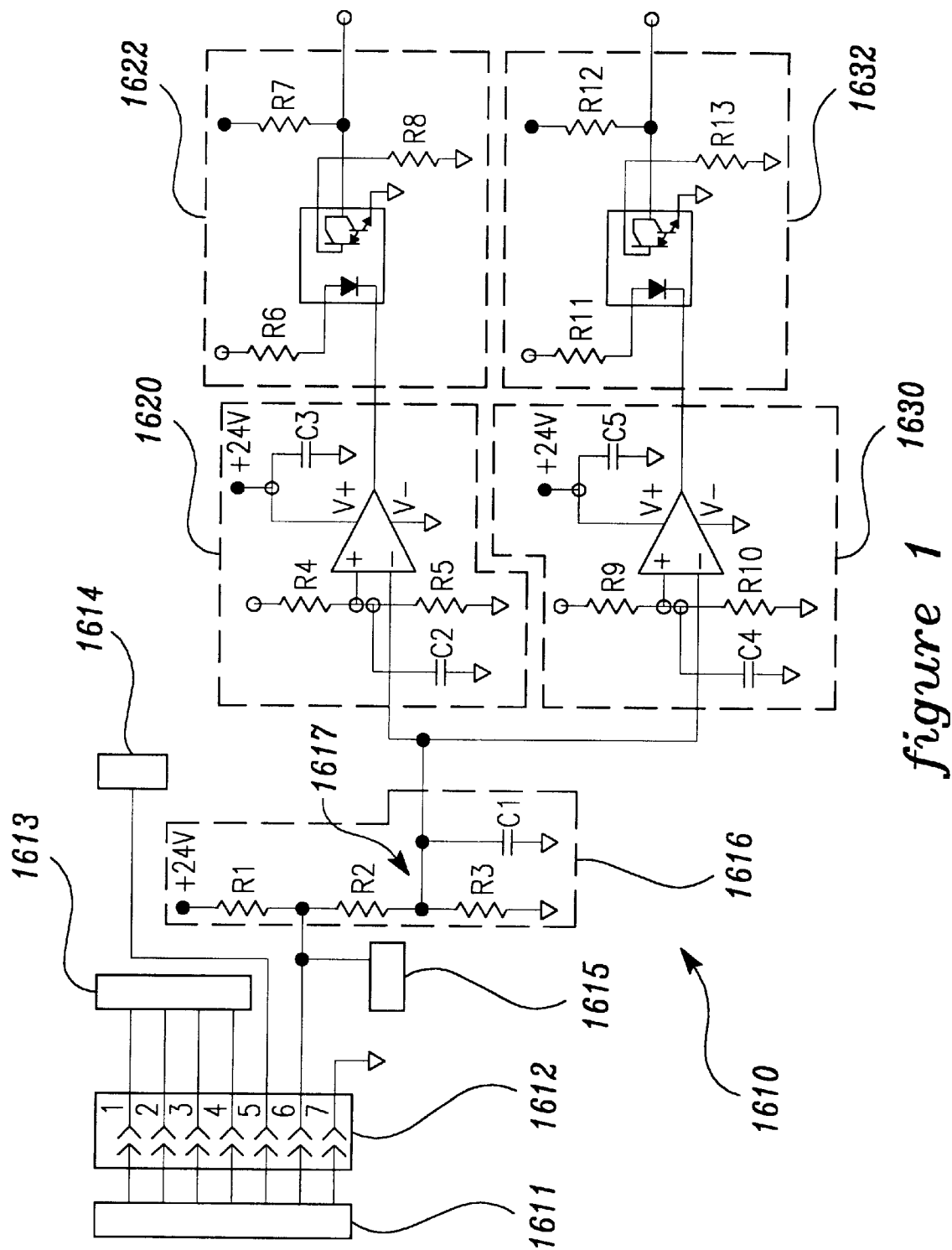
FIG. 1 is an illustration of the intraocular surgical scissors detection apparatus of the present invention.

Turning to the drawing, FIG. 1 illustrates the apparatus of this embodiment of the present invention. The intraocular surgical scissors handpiece motor type detection apparatus is designated generally by the number 1610. A scissors handpiece 1611 is connected to electrical power, the control system and detection apparatus 1610 through connector 1612. Power source 1613 provides electrical power through pins 1–4 in connector 1612 to operate proportional control motor or stepping motor type handpieces 1611. Power source 1614 provides electrical power through pin 5 in connector 1612 to operate solenoid type handpieces 1611. Power source 1615 is connected to pin 6 of connector 1612 and to detection circuit 1610 to provide a signal or bias to the components of detection circuit 1610 when no handpiece 1611 is connected at connector 1612. Pin 7 of connector 1612 is connected to ground. The plug used to connect or mate the handpiece 1611 to connector 1612 must include the required number of pins to conduct electrical power to the handpiece and a shorting bar to complete the circuit between at least two pins of the plug as described hereinafter. The output signals from power sources 1613 and 1614 are controlled by the software of the control system and by other devices such as, for example, foot pedals operated by the surgeon (not shown). Voltage divider 1616 has resistors R1, R2 and R3 connected in series between a 24 volt direct current source and ground and a capacitor C1 is connected in parallel with resistor R3. These components have the following preferred values:

R1=10k ohms
R2=10k ohms
R3=2k ohms
C1=0.1 μfarads

Pin 6 of connector 1612 and power source 1615 are connected to voltage divider 1616 between resistors R1 and R2. The end 1617 of resistor R3 and capacitor C1, the end opposite their connection to ground, is connected to the negative input of first amplifier 1620 and to the positive input of second amplifier 1630 to provide a different bias on each amplifier.

First amplifier 1620 has a typical, well known amplifier configuration. The output from voltage divider 1616 is connected to the negative input of first amplifier 1620. The positive input of first amplifier 1620 is connected to resistors R4 and R5 and to capacitor C2. Resistors R4 and R5 form a voltage divider between an applied amplifier bias voltage and ground and capacitor C2 is connected in parallel with resistor R5 between the positive input of first amplifier 1620 and ground. A 24 volt direct current source is connected to amplifier connection V+ and to ground through capacitor C2 and amplifier connection V− is connected to ground. The components of first amplifier 1620 have the following preferred designations and values:

amplifier=LM393
R4=22.1k ohms
R5=10k ohms
C2=0.1 μfarads
C3=0.1 μfarads

The output of first amplifier 1620 is the input used to excite the light emitting diode of first opto-isolator 1622. When it is excited, first opto-isolator 1622 emits a visual light signal to the receiver portion of its circuit which, in turn, provides a signal to the software control program indicating that a proportional control or stepper motor type of scissors handpiece 1611 has been connected to the detection device 1610. The output of first amplifier 1620 is connected to the cathode of the light emitting diode and resistor R6 is connected between an applied bias voltage and the anode of the light emitting diode. Resistors R7 and R8 are connected in the output of first opto-isolator 1622. The components of first opto-isolator 1622 have the following preferred designations and values:

opto-isolator=4N32
R6=1k ohms
R7=10k ohms
R8=10k ohms

The description of second amplifier 1630 is similar to that of first amplifier 1620 except that the input from voltage divider 1616 is connected to the positive input of second amplifier 1630. Second amplifier 1630 has a typical, well known amplifier configuration. The output from voltage divider 1616 is connected to the positive input of second amplifier 1630. The negative input to second amplifier 1630 is connected to resistors R9 and R10 and to capacitor C4. Resistors R9 and R10 form a voltage divider between an applied amplifier bias voltage and ground and capacitor C4 is connected in parallel with resistor R10 between the negative input to second amplifier 1630 and ground. A 24 volt direct current source is connected to amplifier connection V+ and to ground through capacitor C5 and amplifier connection V− is connected to ground. The components of second amplifier 1630 have the following preferred designations and values:

amplifier=LM393
R9=10k ohms
R10=22.1k ohms
C4=0.1 μfarads
C5=0.1 μfarads

The output of second amplifier 1630 is the input used to excite the light emitting diode of second opto-isolator 1632. When it is excited, second opto-isolator 1632 emits a visual light signal to the receiver portion of its circuit which, in turn, provides a signal to the software control program indicating that a solenoid motor type of scissors handpiece 1611 has been connected to the detection device 1610. The output of second amplifier 1630 is connected to the cathode of the light emitting diode and resistor R11 is connected between an applied bias voltage and the anode of the light emitting diode. Resistors R12 and R13 are connected in the output of second opto-isolator 1632. The components of second opto-isolator 1632 have the following preferred designations and values:

opto-isolator=4N32
R11=1k ohms
R12=10k ohms
R13=10k ohms

In operation of the detection apparatus 1610, when no scissors handpiece 1611 is connected at connector 1612, pin 6 of the connector 1612 is open and power source 1615 provides a small direct current voltage, a voltage of approximately 2.4 volts for example, to voltage divider 1616. This voltage provides neutral bias as it is insufficient to forward bias either first amplifier 1620 or second amplifier 1630. Thus, the control software will indicate that there is no handpiece connected.

When a scissors handpiece 1611 having a proportional control or stepper motor type of drive is connected to connector 1612, pin 6 of connector 1612 is shorted to pin 5 by a shorting bar in the handpiece 1611. When pins 5 and 6 are shorted, the voltage provided by power source 1614 is added to the voltage provided by power source 1615 to provide a higher direct current voltage, a voltage of approximately 4.4 volts for example, to voltage divider 1616. This higher voltage is sufficient to forward bias first amplifier 1620 to provide a signal to first opto-isolator 1622 which in turn provides a signal to the control software. The control software provides a signal to the surgeon visually and, if desired, by creating a noise such as a bell or buzzing sound to advise the surgeon that the connected handpiece 1611 has a stepper motor type of drive and that controls compatible with that drive must be used.

Similarly, when a scissors handpiece 1611 having a solenoid type of drive is connected to connector 1612, pin 6 of connector 1612 is shorted to pin 7 (ground) by a shorting bar in the handpiece 1611. When pins 6 and 7 are shorted, pin 6 is shorted to ground and the voltage provided to voltage divider 1616 is zero. This lower voltage is creates a forward bias on second amplifier 1630 which provides a signal to second opto-isolator 1632 which in turn provides a signal to the user interface control software. The control software provides a signal to the surgeon visually and, if desired, by creating a noise such as a bell or buzzing sound to advise the surgeon that the connected handpiece 11 has a solenoid type of drive and that controls compatible with that drive must be used.

It should be recognized that the selected values for resistors, capacitors and other components and for stated voltages are provided for illustration of the invention and not as the only combination and that the values of each or the components may be changed without changing the invention.

The present invention further includes a method for determining the type of motor control required for a connected handpiece such as the preferred intraocular surgical scissors handpiece. The method includes the steps of applying a voltage across a voltage divider to the input of a first and a second amplifier, connecting a handpiece, changing the voltage across the voltage divider indicative of the handpiece motor drive type, forward biasing one of the first and second amplifiers as a result of changing the voltage across the voltage divider and providing a signal to the control system indicative of the handpiece motor drive type. The method may also include providing a visual indication of the handpiece motor drive type.

In view of the foregoing, it will be seen that several advantages are attained.

Although the foregoing includes a description of the best mode contemplated for carrying out this embodiment of the invention, various modifications are contemplated.

As various modifications could be made in the constructions herein described and illustrated without departing from the scope of the invention, it is intended that all material contained in the foregoing description or shown in the accompanying drawings should be interpreted as illustrative rather than limiting.

What is claimed is:

1. An apparatus for determining the motor type of an electric intraocular surgical handpiece in combination with an electric intraocular surgical handpiece connected thereto comprising:

a voltage divider for receiving a signal indicative of the motor type of said connected electric intraocular surgical handpiece;

first and second amplifiers for receiving a bias voltage from the voltage divider, one of the first and second amplifiers being forward biased providing a signal indicative of the handpiece motor type.

2. The apparatus of claim 1 further including first and second opto-isolators which receive a signal from the first and second amplifiers respectively and control software which receives a signal from the first or second opto-isolator and provides a visual signal indicative of the motor type of said connected handpiece.

3. A method for determining the motor type of an electric intraocular surgical handpiece comprising:

applying a voltage across a voltage divider to the input of a first and a second amplifier, connecting said handpiece to a connector that is in electrical communication with said voltage divider, changing the voltage across the voltage divider indicative of said handpiece motor drive type, forward biasing one of the first and second amplifiers as a result of changing the voltage across the voltage divider, and providing a signal to the control system indicative of the handpiece motor drive type.

4. The method of claim 3 further including providing a visual indication of the handpiece motor drive type.

* * * * *